(12) United States Patent
Okita et al.

(10) Patent No.: US 7,627,241 B2
(45) Date of Patent: Dec. 1, 2009

(54) IMAGE PICK-UP INSPECTION EQUIPMENT AND METHOD

(75) Inventors: Takanori Okita, Tokyo (JP); Kouichi Suzuki, Tokyo (JP)

(73) Assignee: Renesas Technology Corp., Tokyo (JP)

(*) Notice: Subject to any disclaimer, the term of this patent is extended or adjusted under 35 U.S.C. 154(b) by 500 days.

(21) Appl. No.: 11/263,917

(22) Filed: Nov. 2, 2005

(65) Prior Publication Data

US 2006/0170911 A1     Aug. 3, 2006

(30) Foreign Application Priority Data

Dec. 21, 2004   (JP) ............................. 2004-370052

(51) Int. Cl.
*G03B 15/03* (2006.01)
*G01N 21/00* (2006.01)
*H04N 7/18* (2006.01)

(52) U.S. Cl. ................. 396/155; 396/505; 348/87; 348/126; 250/559.34; 356/237.5

(58) Field of Classification Search .............. 396/505, 396/155; 348/87, 126; 250/559.34; 356/237.5
See application file for complete search history.

(56) References Cited

U.S. PATENT DOCUMENTS 5,365,341 A * 11/1994 Sugawara .................... 356/394
6,161,753 A * 12/2000 Tsai et al. ................ 228/180.5

FOREIGN PATENT DOCUMENTS

JP           5-160230           6/1993

* cited by examiner

*Primary Examiner*—W B Perkey
(74) *Attorney, Agent, or Firm*—Oblon, Spivak, McClelland, Maier & Neustadt, L.L.P.

(57) ABSTRACT

An objective lens system opposing an imaged surface of semiconductor device, and imaging lens system arranged between this objective lens system and image sensor is used to inspect a lower component of the semiconductor device without being influence by an upper component. The F value of objective lens system is made into 1.5 or less, and an imaged surface is photographed and inspected. The imaging lens system also has several lenses with different focal distances. According to the desired magnification, a predetermined lens among the plurality of lenses is arranged in the predetermined location of an optical axis, and the other lenses are evacuated from an optical axis.

11 Claims, 8 Drawing Sheets

IMAGE PICK-UP INSPECTION EQUIPMENT AND METHOD

CROSS-REFERENCE TO RELATED APPLICATION

The present application claims priority from Japanese patent application No. 2004-370052 filed on Dec. 21, 2004, the content of which is hereby incorporated by reference into this application.

FIELD OF THE INVENTION

This invention relates to the image pick-up inspection equipment and the method of picturizing and inspecting the imaged surface of a semiconductor device.

DESCRIPTION OF THE BACKGROUND ART

In the manufacturing process of a semiconductor device, it is necessary to inspect the shape or its arrangement of the bonding pad of a chip main surface, a ball, etc. The inspection method of the shape of a ball and the device used for it are indicated by Japanese Unexamined Patent Publication No. Hei 5-160230 (Reference 1). In 0024-0025 paragraphs of this Reference 1, the method of making reflected light from the wire not being a photography object a faded image, and projecting brightly only the ball being an object for photography by further opening the diaphragm of an optical system wide and making shallow depth of focus (depth of field) after lessening incidence to the objective lens of the reflected light from a semiconductor chip main surface as much as possible by using the illumination from low irradiation angles with a low irradiation-angles ring shape illuminator, is indicated.

[Patent Reference 1] Japanese Unexamined Patent Publication No. Hei 5-160230

SUMMARY OF THE INVENTION

As a trend of the latest semiconductor package, the inclination of chip lamination and the pitch reduction of a wire bonding pad has become strong. As a result, the packages with which a wire crossed over the ball on the surface of a chip were increasing in number. If an image is picturized with a camera from the upper part when inspecting the subject of examination (ball) located under the wire, a wire up in the air will be picturized simultaneously, and the test was difficult.

The problem of the defect by relative location gap of a ball and a wire bonding pad is also becoming serious by performing reduction of the pitch of a wire bonding pad. And when inspecting a ball, inspecting simultaneously not only inspection of the shape of a ball but the relative spatial relationship of a ball and a bonding pad is called for.

In order to inspect the relative spatial relationship of a ball and a bonding pad, it is the most effective to measure a relative location gap of the image of a ball and the image of a chip main surface using bright field illumination, as both the reflected light from a ball and the reflected light from a chip main surface enter into an objective lens. However, since it is difficult to keep the reflected light from the wire being up from entering into an objective lens when using bright field illumination, the measures keeping from doing the serious trouble for photography about the reflected light from the upper wire not being a photography object are demanded simultaneously.

When a level difference (location gap of an optical axis direction) exists between the photography obstruction (upper part wire) and the photography object (ball), as 0024-0025 paragraphs of Reference 1 have disclosure, by making the depth of field of an imaging surface shallow, it becomes possible to make reflected light from a photography obstruction into a faded image and project only the object for photography vividly. However, when photography objects are both a ball, and a chip main surface, the level difference of an optical axis direction arises on the surface of a photography object. The fading of an image by the reflected light from a photography object surface becomes large as a depth of field is made shallow when a level difference is shown in the surface of a photography object.

Fading of this image is explained with reference to FIG. 1 and FIG. 2. FIG. 1 is a top view showing the relation between ball a, wire b, and pad c. The boundary of ball a and pad c is made into Q point, the location to the drawing left is made into P point, and the location to the right is made into R point like illustration. FIG. 2 shows the lightness profile of the image which picturized the structure of FIG. 1. An axis of abscissa is the distance from boundary point Q to a horizontal direction, an axis of ordinate shows the lightness of an image, lightness Ma is the lightness of ball a, lightness Mc is the lightness of pad c, and image Mm is the lightness of both median.

Image A shows the case where there is no image fading. Image blurring arises in image B, and lightness changes from boundary point Q to a left by distance B1, to a right by distance B2, and this region turns into a fading region. Image blurring arises further in image C, and it turns into a fading region from boundary point Q to a left by distance C1, to a right by distance C2.

Now, if the lightness range by plus or minus $\Delta M$ from median Mm of lightness Ma and Mc of an image is the error range of the threshold of a boundary judging, as illustrated, as to the error range of a boundary judging, it becomes a size of plus or minus $\Delta B$ in the case of image B, and it becomes a size of plus or minus $\Delta C$ in the case of image C. Thus, if image fading becomes large, a borderline will fade and the distinction error of a boundary point will become large.

When a level difference (location gap of an optical axis direction) exists between the photography obstruction (upper part wire) and photography object (ball), as 0024-0025 paragraphs of Reference 1 have disclosure, by making the depth of field of an imaging surface shallow, it becomes possible to make reflected light from a photography obstruction into a faded image and project only the object for photography vividly. However, when photography objects are both a ball, and a chip main surface, the level difference of an optical axis direction arises on the surface of a photography object. Fading of the image of the reflected light from a photography object surface becomes large as a depth of field is made shallow, when a level difference is shown in the surface of a photography object.

As mentioned above, in inspection on the surface of a chip, while making reflected light from the photography obstruction (wire) being up the faded image, it is necessary to project as vividly as possible both the balls, and the chip main surface of photography objects existing below the photography obstruction.

Based on such an issue examined uniquely, the present inventors examined the optimal F value of the objective lens system that can make the reflected light from the upper part wire being a photography obstruction fully fade, and that can put in the reflected light from both sides of the ball and the chip main surface being photography objects within the limits of allowance fading, and it resulted in the present invention.

An image pick-up inspection equipment and method of a semiconductor device concerning this invention comprises an objective lens system opposing an imaged surface; and an imaging lens system arranged between the objective lens system and an image sensor; wherein an F value of the objective lens system is below the F value with which image fading of an upper wire becomes 5 or more times of a wire diameter making the semiconductor device surface into a focal plane.

An image pick-up inspection equipment and method of a semiconductor device concerning this invention comprises an objective lens system opposing an imaged surface; and an imaging lens system arranged between the objective lens system and an image sensor; wherein an F value of the objective lens system is 1.5 or less.

Other image pick-up inspection equipments and methods of a semiconductor device concerning this invention comprise an objective lens system opposing an imaged surface; and an imaging lens system arranged between the objective lens system and an imaging surface; wherein the imaging lens system has a plurality of lenses with which focal distances differ, arranges a predetermined lens among the plurality of lenses in a predetermined location of an optical axis according to a desired magnification, and evacuates other lenses from the optical axis. The other features of this invention are explained further below.

According to this invention, even when component parts lap up and down spatially on the surface of a semiconductor device, without being influenced by upper components, an image pick-up and inspection of lower components can be conducted. Especially even if there are a plurality of lower part articles and there is a fixed vertical interval, an image pick-up and inspection of a plurality of lower part articles can be conducted.

Even if the wire intersects the bonding pad and the ball of lower part articles as an example after the wire bonding step connecting a semiconductor chip and a lead frame, image pick-up inspection of shape, spatial relationship, etc. of the bonding pad and the ball can be conducted.

DETAILED DESCRIPTION OF THE PREFERRED EMBODIMENTS

Embodiment 1

Figure 1:
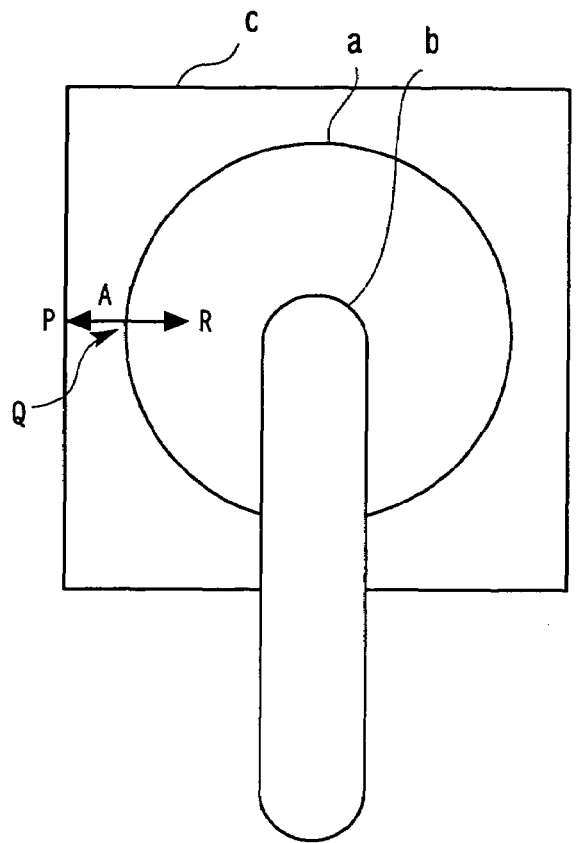
FIG. 1 is a top view of the ball part on the surface of a chip of a semiconductor device.
Figure 2:
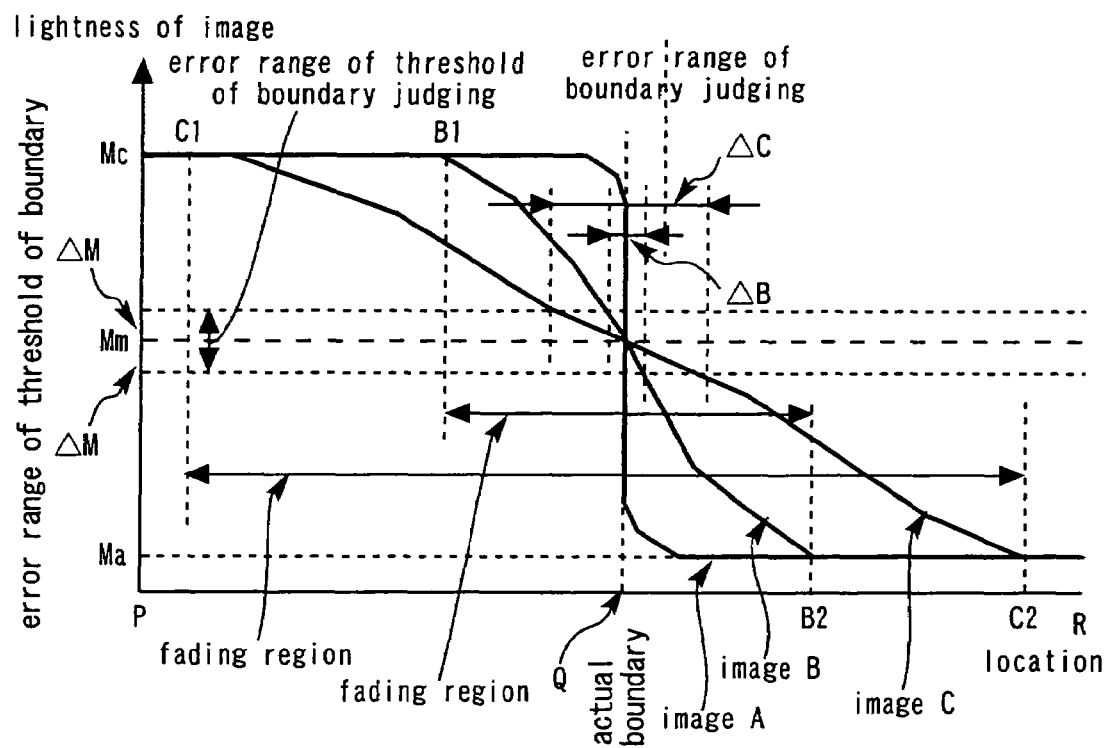
FIG. 2 is a drawing showing the lightness profile of the picked-up image on the surface of a chip.
Figure 3:
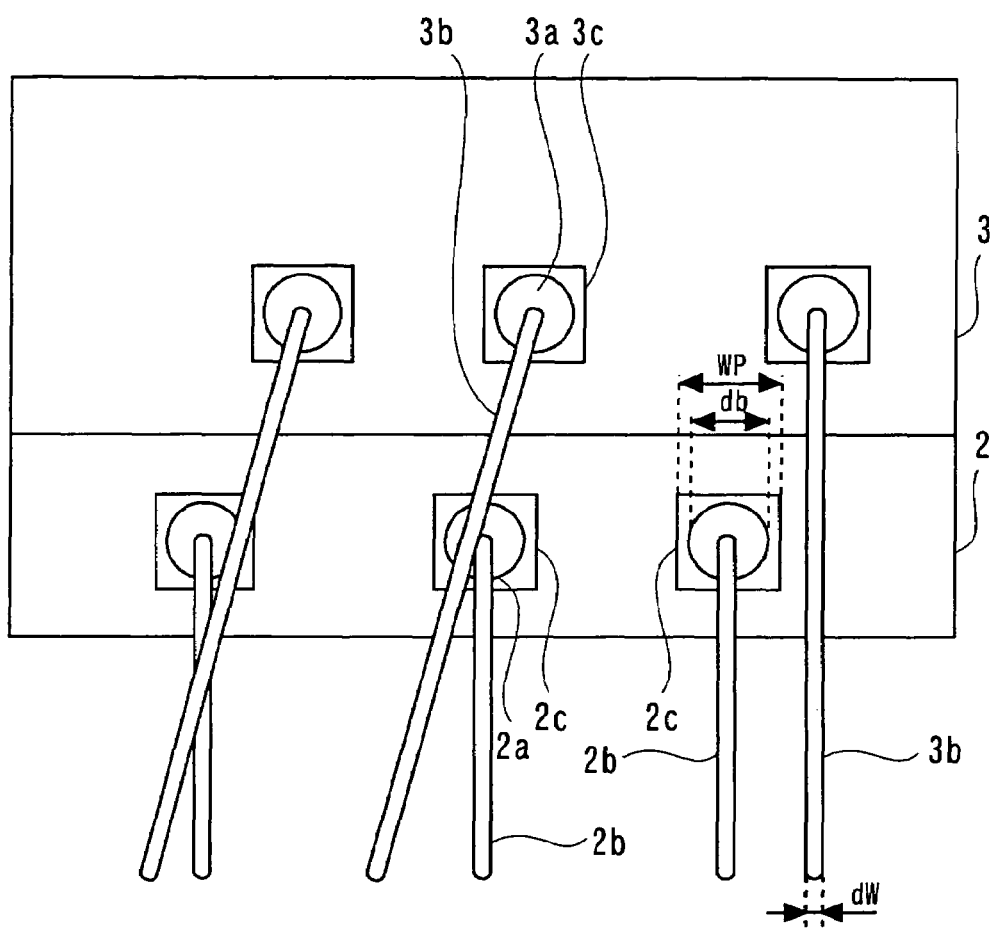
FIG. 3 is a chip top view of a semiconductor device made into an example to be examined in this embodiment of the invention.
Figure 4:
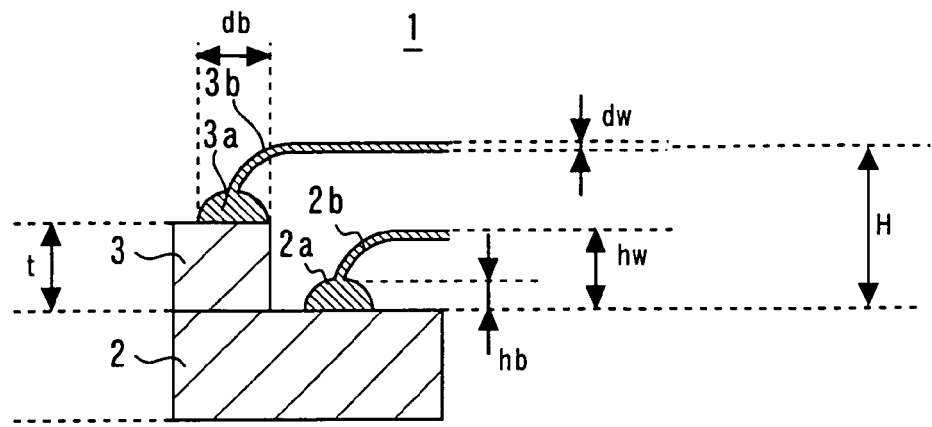
FIG. 4 is a sectional view of a semiconductor device made into an example to be examined in this embodiment of the invention.

FIG. 3 is an example of the chip top view of a semiconductor device, and FIG. 4 shows the sectional view of a part where an upper wire crosses the upper air of a downward ball in a semiconductor device like FIG. 3. A structure part as shown in this FIG. 4 considers it as an example to be examined in the embodiment of this invention.

Stacked chip type semiconductor device 1 of FIG. 3 or FIG. 4 stacks in layers upper chip 3 on lower chip 2. Ball 2a is formed in surface bonding pad 2c, and lower chip 2 has wire 2b connected to this ball 2a. Ball 3a is formed in surface bonding pad 3c, and upper chip 3 has wire 3b connected to this. The chip thickness of up-and-down chips 2 and 3 is shown by t, WP shows the pad width of bonding pads 2c and 3c, db shows the diameter of balls of 2a and 3a, hb shows ball height, dw shows a wire gage, and hw shows the wire height from the chip surface of up-and-down chips 2 and 3. And the height from the surface of lower chip 2 to the center of wire 3b of upper chip 3 is shown by H.

Lower wire 2b is a wire connecting lower chip 2 and a lead terminal (located out of a drawing). Lower ball 2a is a ball formed when connecting lower chip 2 and lower wire 2b by wire bonding, and let it be an image pick-up object by the Embodiment.

Upper wire 3b is a wire connecting upper chip 3 and other lead terminal (located out of a drawing), and is in the location crossing the vertical upper part of lower ball 2a.

By the embodiment, the surface or the imaged surface of such a semiconductor device 1 is made into an example to be examined, and especially the example to conduct the image pick-up and inspection of lower bonding pad 2c and lower ball 2a being located directly under upper wire 3b is explained.

In semiconductor device 1 shown in FIG. 4 here, usually, wire gauge dw is φ20–30 μm, ball diameter db is φ50–120 μm, chip thickness t is 50–400 μm, wire height hw is 80–400 μm, and ball height hb is about 20–50 μm.

And, in the following, considering the dimension as following passages, discussion is performed.

Bonding-pad Width WP: 55 μm,
Wire Diameter dw: 25 μm,
Ball Diameter db: 45 μm,
Ball Height hb: 15 μm,
Height H from a chip main surface to an upper wire center: 150 μm.

Figure 5:
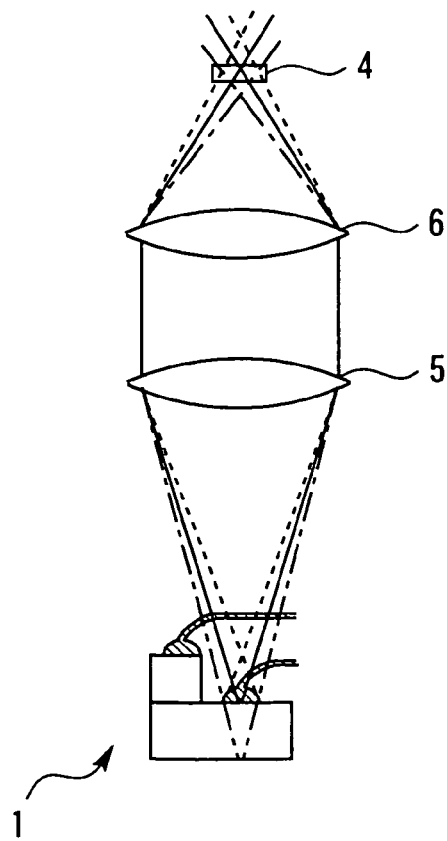
FIG. 5 is a drawing showing the outline structure of the image pick-up inspection equipment which picturizes and inspects the imaged surface of a semiconductor device, in Embodiment 1 of this invention.

FIG. 5 is a drawing showing the outline structure of the image pick-up inspection equipment which picturizes and inspects the imaged surface of a semiconductor device in the embodiment. The image pick-up inspection equipment of this embodiment is provided with image sensor 4, objective lens system 5 which opposes the imaged surface of semiconductor device 1, and imaging lens system 6 arranged between this objective lens system 5 and image sensor 4 at least. Although not illustrated, it has the illumination means which performs coaxial illumination of the semiconductor device 1 by a bright field with coaxial illumination with the visible light of wave length 400-700 nm.

Image sensor 4 includes a CCD camera, a line camera, etc. Objective lens system 5 includes image formation elements, such as an optical lens located in the side of an image pick-up object.

By the way, the F value of a lens system is decided by the construction material of a lens system including an objective lens system and an imaging lens system, shape, the wave length from an illuminant, etc. In the case of the optical design to which image-formation of all the lights that entered into the objective lens system from the image pick-up object especially is performed by the imaging lens system, the F value of the whole lens system is determined by the F value of an objective lens system. A depth of field is decided by the F value of a lens system, and allowance fading. In the embodiment, in order to obtain sufficient aperture ratio, a depth of field can be acquired by the F value of an objective lens system, and allowance fading for the optical design to which image-formation of all the lights that entered into the objective lens system from the image pick-up object is performed by the imaging lens system. Each lens system may include two or more lenses.

Figure 6:
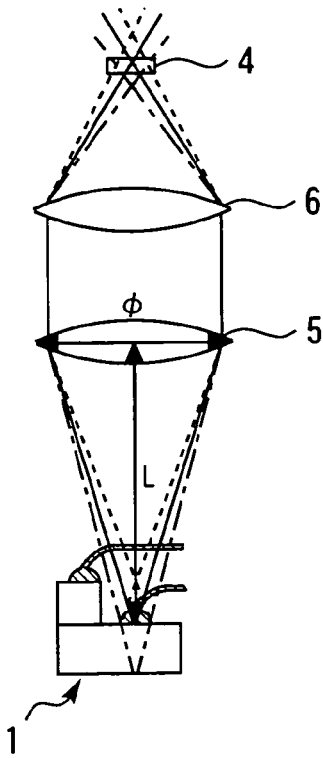
FIG. 6 is a drawing for explaining the F value of an imaging system.

The F value and the amount of fading are explained here. In the imaging system shown in FIG. 6, if the effective aperture diameter of an objective lens is set to $\Phi$ and the focal distance from an objective lens is set to L, F value=$L/\Phi$, i.e., an F value, will be defined as the value which divided the distance (focal distance) from an objective lens to a focus by the effective aperture diameter of the objective lens.

Figure 7:
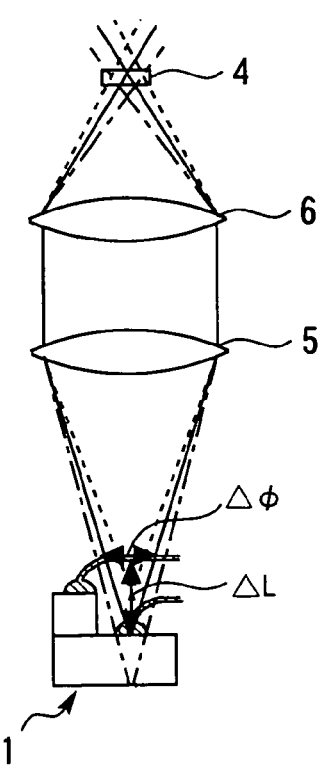
FIG. 7 is a drawing for explaining the amount of fading of an imaging system.

In the imaging system shown in FIG. 7, when the diameter of the blur circle in the height of an upper part wire is set to $\Delta\Phi$ and the distance from a focus is set to $\Delta L$, an F value is $\Delta L/\Delta\Phi$. At this time, amount of fading=$\Delta\Phi/2$, i.e., the amount of fading is defined as the radius of a blur circle.

Now, about the upper part wire being a photography obstruction, it is preferred to choose the range of an F value where the image fades to 5 or more times of an original wire diameter. That is, it is preferred to choose the range of an F value where fading (=the radius of a blur circle) in an upper part wire position becomes 2 or more times of wire diameter dw.

(1) Example of fading of an upper part wire:
  Focal plane=chip main surface
  Distance from the focal plane of an upper part wire (wire height H)=150 μm
    Wire diameter (dw)=25 μm
    Desirable radius of a blur circle$\geq$wire diameter (dw)$\times$2=50 μm
    Radius of a blur circle$\times$2=the distance from focal plane/F value
    Calculating from the above-mentioned values, it will be set to desirable F value Max$\leq$1.5.

Next, about the chip main surface and the ball which are photography objects, when a focal plane is doubled with a chip main surface, it is preferred that image fading of a ball has fallen within a certain amount of range to the distance of a ball and a bonding pad end portion. The present inventors, as a result of analyses, found out that, by fitting image fading of a ball in 2 or less times, preferably in 1.5 or less times at the maximum to the distance of a ball and a bonding pad end portion, the location gap to a bonding pad of a ball could be judged in sufficient accuracy.

As for the distance here of a ball and a bonding pad end portion, assuming the case where the ball has been arranged at the center of a bonding pad, the value calculated by the difference of a radius of the ball and (pad width/2) is defined as the par distance of a ball and a bonding pad end portion.

In the following example, when calculating on the conditions to which image fading in the top face being distant from a focal plane of a ball is settled in 2 or less times to the par distance of a ball and a bonding pad end portion, desirable F value Min is as follows.

(2) Example of fading of a ball top face:
  Focal plane=chip main surface
  Distance from a focal plane to the top face of a ball (ball height hb)=15 μm
    Ball diameter db=45 μm
    Bonding pad width WP=55 μm
    Desirable radius of a blur circle$\leq$(WP-db)$\times$(1/2)$\times$2=10 μm
    It is set to desirable F value Min$\geq$0.75.

In the following example, when calculating on the conditions to which image fading in the top face being distant from a focal plane of a ball is settled in 1.5 or less times to the par distance of a ball and a bonding pad end portion, more desirable F value Min is as follows.

(3) Example of fading of a ball top face:
  Focal plane=chip main surface
  Distance from a focal plane to the top face of a ball (ball height hb)=15 μm
    Ball diameter db=45 μm
    Bonding pad width WP=55 μm
    Desirable radius of a blur circles$\leq$(WP-db)$\times$3/4=7.5 μm
    Calculating from the above-mentioned values, it is set to F value Min$\geq$1.

It is as follows when above examples (1)-(3) are summarized.
  (1) F valueMax$\leq$1.5
  (2) F valueMin$\geq$0.75
  (3) F valueMin$\geq$1

Therefore, it is set to 1.5$\geq$F value Max, and F value Min$\geq$1$\geq$0.75.

From the above things, while making reflected light from the photography obstruction (wire) in the upper part the faded image and making it there be no fault, in order to project so that both a ball and a chip main surface of the photography object existing below can be inspected, the range of a desirable F value is 1.5$\geq$F value$\geq$0.75, and is set to 1.5$\geq$F value $\geq$1 still more desirably.

In order to fully demonstrate the capacity of an image processing system and an optical system, as for the amount of fading in a ball top face, it is preferred to hold down to the suitable range to image resolving power, for example, the amount of fading is preferred to hold down to 5 or less times of image resolving power.

(4) Example of fading of a ball top face:
  Focal plane=chip main surface
  Distance from a focal plane to the top face of a ball (ball height hb)=15 μm
    Image resolving power=2 μm
    Amount of allowance fading$\leq$2$\times$5=10 μm
    It is set to desirable F value Min$\geq$15/(10$\times$2)=0.75.

The above-mentioned example (2) and the result of this correspond.

Figure 8:
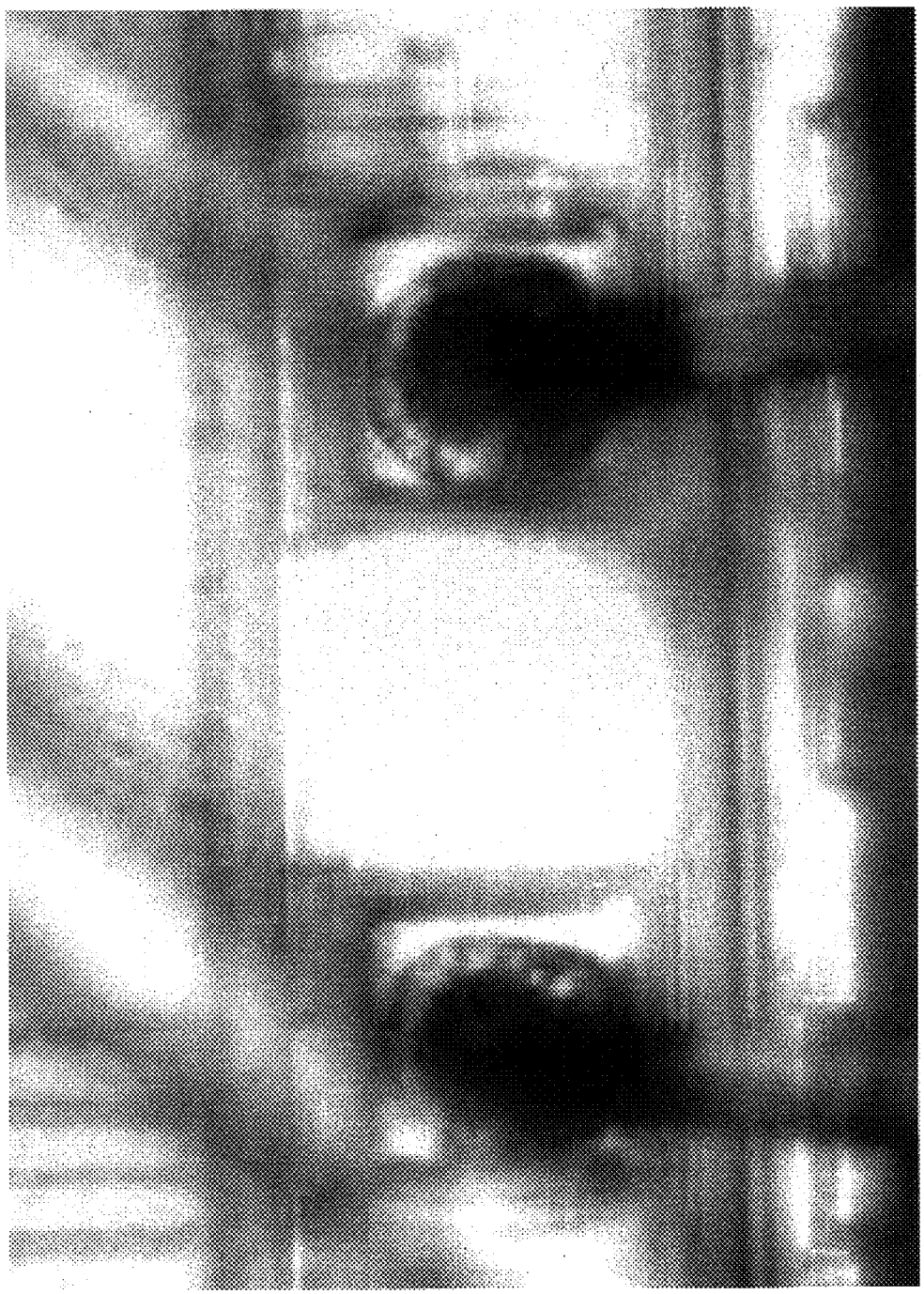
FIG. 8 shows the picked-up image of the imaged surface of a semiconductor device, by Embodiment 1 of this invention.
Figure 9:
FIG. 9 shows the picked-up image for a comparison.
Figure 10:
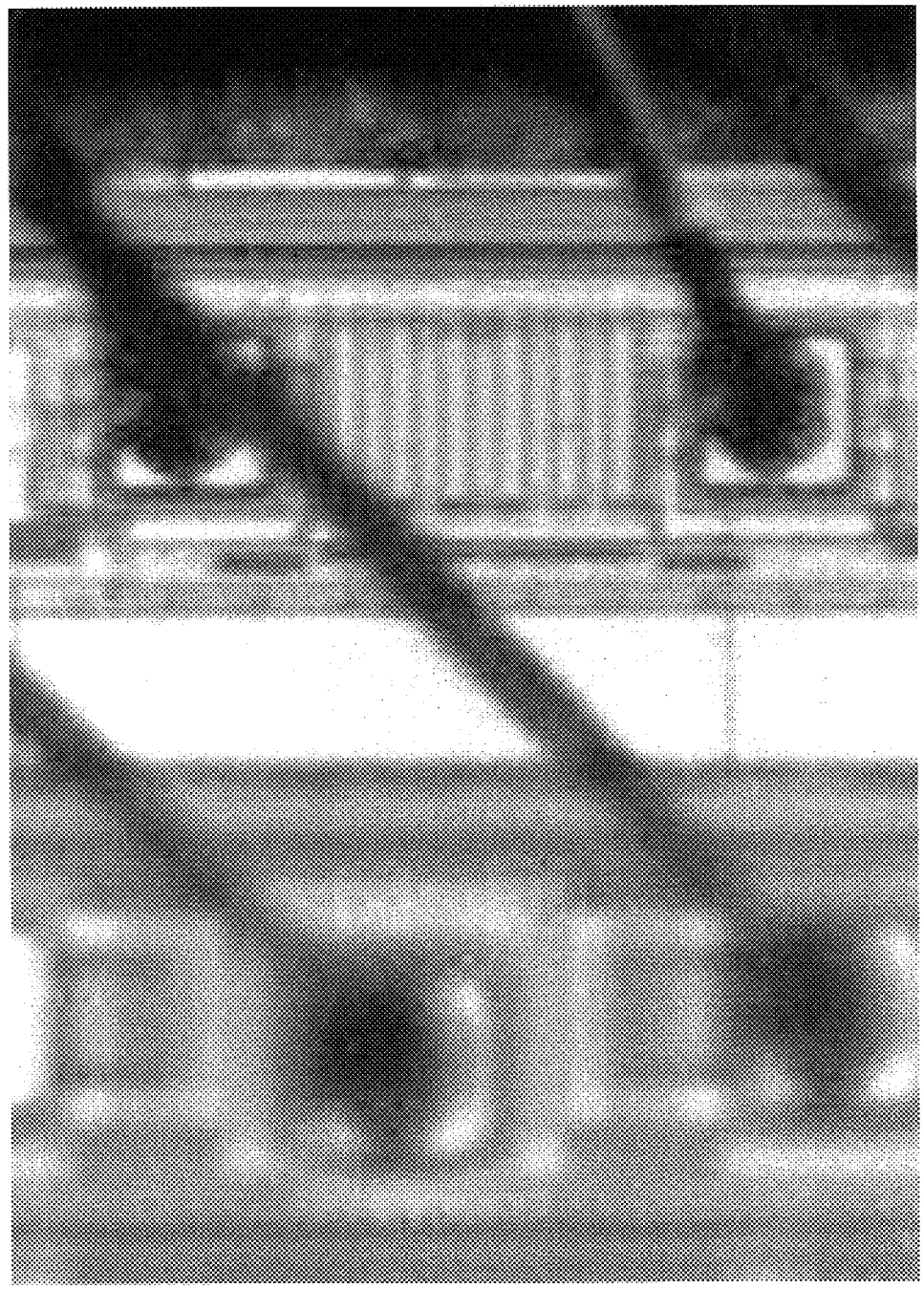
FIG. 10 shows other picked-up images for a comparison.

FIG. 8 shows the picked-up image which actually picturized the chip surface. FIG. 9 and FIG. 10 show the picked-up image for a comparison. F value=1.4 in FIG. 8, F value=1.8 in FIG. 9, and F value=2.8 in FIG. 10. In FIG. 8, it turns out that the image which has not been substantially influenced by the upper wire was obtained, and it is influenced by an upper wire in FIG. 9 and FIG. 10.

As mentioned above, when the vertical interval of wire 3b, and lower bonding pad 2c and lower ball 2a which lapped up and down is 150 μm or more in the embodiment, by using objective lens system 5 designed by 1.5 or less in the F value, even when the bright field illumination by coaxial illumination with the visible light of wave length 400-700 nm was used, it became possible to obtain the image of lower bonding pad 2*c* and lower ball 2*a*, after fully reducing the effect of upper wire 3*b*.

In the embodiment, although having made the case where a lower ball was inspected into the example, about the case where other parts such as a stitch-bonding side and a middle wire are picturized, it is also same.

In the embodiment, although indicating about the example of desirable F value Max calculated as a result of discussing with the application of a specific dimension based on the concept of invention of choosing the F value to which the image of the upper part wire being a photography obstruction fades to 5 or more times of a wire diameter, as an embodiment of the invention, it does not restrict above. Of course, it is also possible to apply to the step inspecting the semiconductor device of another dimension based on the concept of an above-mentioned invention. As a result of examining the inspection step of the semiconductor device of another dimension based on the concept of the above-mentioned invention, desirable F value Max may differ from desirable F value Max indicated by the embodiment.

The same may be said of the concept of invention of choosing the F value to which image fading in a ball top face is settled in twice or less, more preferably 1.5 or less times of the par distance of a ball and a bonding pad end portion. Of course about the object of application of an invention, not restricting to the case of the specific dimension indicated by the embodiment, it is also possible to apply to the step inspecting the semiconductor device of another dimension. In another dimension, desirable F value Min may differ from desirable F value Min indicated by the embodiment.

As mentioned above, in the present invention, when it is going to picturize imaged surfaces, such as a bonding pad on the semiconductor device surface or the surface of a chip, and a ball on it fully reducing the effect of photography obstructions, such as a wire crossing the upper air, as an F value of the objective lens system opposing an imaged surface, below the F value from which image fading of the upper wire becomes 5 or more times of the wire diameter making the semiconductor device surface into a focal plane is chosen.

When a level difference exists in an imaged surface like the bonding pad on the surface of a semiconductor device, and the ball on it, beyond the F value from which image fading of a ball top face becomes below twice of the difference of the half of the width of the bonding pad and the radius of ball is chosen.

Embodiment 2

Figure 11:
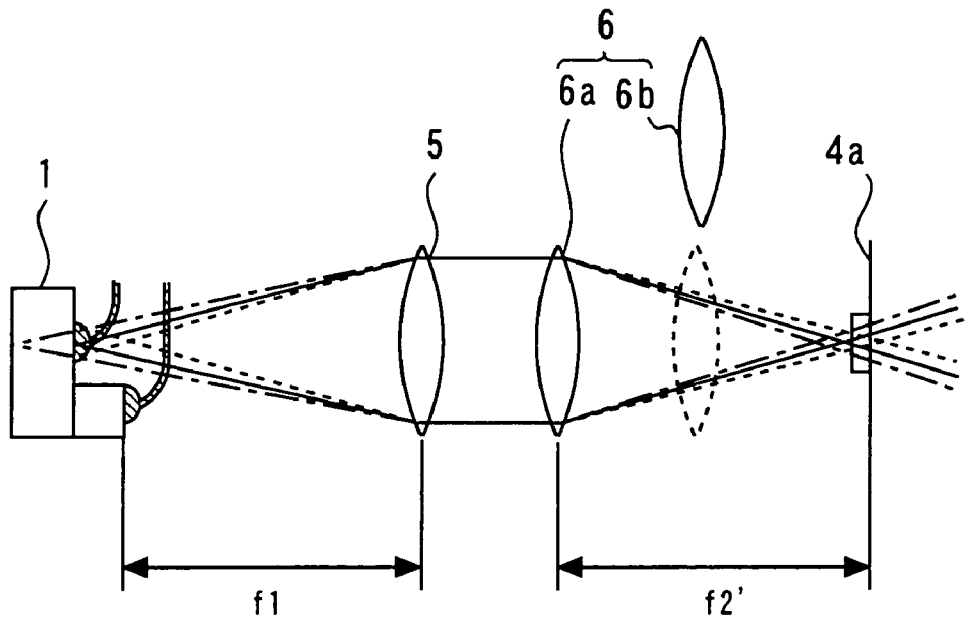
FIG. 11 is a drawing showing the outline structure of the image pick-up inspection equipment which picturizes and inspects the imaged surface of a semiconductor device in Embodiment 2 of this invention, and shows the lens arrangement at the time of high magnification.
Figure 12:
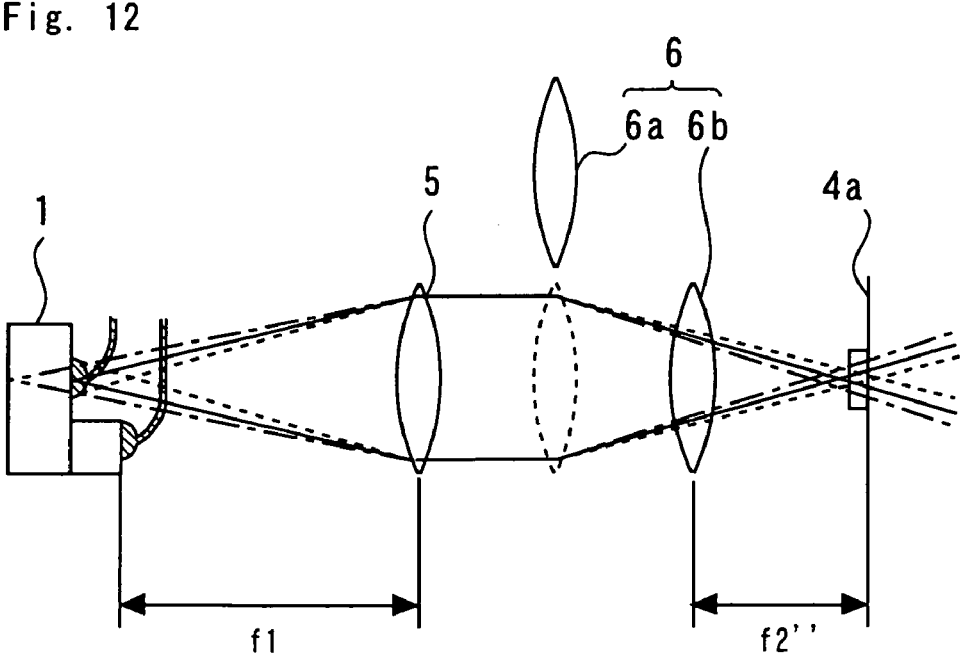
FIG. 12 is a drawing showing the outline structure of the image pick-up inspection equipment which picturizes and inspects the imaged surface of a semiconductor device in Embodiment 2 of this invention, and shows the lens arrangement at the time of low magnification.

FIG. 11 and FIG. 12 are the drawings showing the outline structure of the image pick-up inspection equipment which picturizes and inspects the surface or the imaged surface of a semiconductor device in Embodiment 2 of this invention. FIG. 11 shows the lens arrangement at the time of high magnification, and FIG. 12 shows the lens arrangement at the time of low magnification. The image pick-up inspection equipment of this embodiment is, at least, provided with objective lens system 5 opposing the imaged surface of semiconductor device 1, and imaging lens system 6 arranged between this objective lens system 4 and imaging surface 4*a*. Although not illustrated, it has the illumination means performing coaxial illumination of the semiconductor device 1 by a bright field.

The magnification projected on imaging surface 4*a* is decided by focal distance f1 of objective lens system 5, and focal distance f2 of imaging lens system 6. As objective lens system 5, the lens system turning into a telecentric system from an objective lens system to the imaging surface 4*a* side is used. As imaging lens system 6, it has two or more sheets for image formation lenses 6*a* and 6*b* with which a focal distance is different, for example, a high magnification lens 6*a* (focal-distance f2'), and low magnification lens 6*b* (focal-distance f2"), and enabled it to change the magnification gradually according to the required magnification.

When inspection by high magnification is required, like FIG. 11, high magnification lens 6*a* is arranged on an optical axis, and low magnification lens 6*b* is evacuated. Conversely, in the case of inspection by low magnification, as shown in FIG. 12, high magnification lens 6*a* is evacuated and low magnification lens 6*b* is arranged on an optical axis. A suitable lens can be chosen and an inspection rate can be optimized by changing the magnification according to the required accuracy of an inspection object, as a low magnification lens is used to inspect the large range with low magnification using a high magnification lens to inspect the narrow range with high magnification. After the change as well, inspection can be smoothly performed by giving the calibration data amending the aberration of a lens etc. for each magnification. The number of sheets of the lens of imaging lens system 6*b* may not be restricted in two sheets, but may be suitable number of sheets.

As things mentioned above, the present inventions accomplished by the present inventors were concretely explained based on above embodiments, but the present inventions are not limited by above embodiments, but variations and modifications may be made, of course, in various ways in the limit that does not deviate from the gist.

What is claimed is:

1. An image pick-up inspection method of inspecting a semiconductor device, comprising the steps of:
    performing illumination by a bright field on a surface of the semiconductor device including
        a semiconductor chip having a pad on the surface thereof, and
        a first electrical wire bonded on the pad; and
    imaging the surface of the semiconductor device illuminated by the bright field with an objective lens system opposing the surface of the semiconductor device,
    wherein the objective lens system has an F value of 1.5 or less to establish an image of the pad.

2. An image pick-up inspection method according to claim 1, wherein
    the semiconductor device further includes
    a second electrical wire provided at a higher position than the first electrical wire and not bonded on the pad.

3. An image pick-up inspection method according to claim 2, wherein the semiconductor device further includes at least one other semiconductor chip having a pad on which the second electrical wire is bonded, and the at least one other semiconductor chip is positioned over the surface of the semiconductor chip.

4. An image pick-up inspection method of inspecting a semiconductor device, comprising the steps of:
    illuminating by a bright field a surface of the semiconductor device that includes,
        a first semiconductor chip having a pad on a surface thereof; and
        a first electrical wire being at a higher position than the pad; and imaging the surface of the semiconductor device by the bright field with an objective lens system having an F value corresponding to an image fading of the first electrical wire to 5 or more times a diameter of the first electrical wire to establish an image of the pad.

5. An image pick-up inspection method according to claim 4, wherein the objective lens system has the F value corresponding to an image fading of a top of a ball, which is situated on the pad of the semiconductor device and connected to the first electrical wire, to 2 or less times of a difference of a half of a width of the pad and a radius of the ball.

6. An image pick-up inspection method according to claim 4, wherein the semiconductor device further includes a second electrical wire bonded on the pad while the first electrical wire is not bonded on the pad.

7. The image pick-up inspection method according to claim 4, wherein the semiconductor device further includes a second semiconductor chip having a pad on which the second electrical wire is bonded, and the second semiconductor chip is arranged over the surface of the first semiconductor chip.

8. An image pick-up inspection method according to claim 1, wherein, F value of the objective lens system is 1.0 or more.

9. An image pick-up inspection method of inspecting a semiconductor device, comprising:

illuminating by a bright filed a surface of the semiconductor device that includes a first semiconductor chip and a first electrical wire being provided over a surface of the first semiconductor chip; and imaging the surface of the semiconductor device by the bright field with an objective lens system whose F value is so adjusted to make an image of the first electrical wire faded to an extent that a hidden portion of the surface of the semiconductor chip in an upper view by the first electrical wire is imaged.

10. An image pick-up inspection method according to claim 9, wherein the semiconductor device further includes a second electrical wire bonded on a pad which is provided on the surface of the semiconductor chip and being provided at a position lower than the first electrical wire relatively to the surface of the semiconductor chip.

11. An image pick-up inspection method according to claim 10, wherein the semiconductor device further includes a second semiconductor chip having a pad on which the second electrical wire is bonded, and the second semiconductor chip is arranged over the surface of the first semiconductor chip.

* * * * *